United States Patent [19]

Henkels et al.

[11] Patent Number: 4,879,306

[45] Date of Patent: Nov. 7, 1989

[54] COMPOSITION KILLING OR INHIBITING THE GROWTH OF MICROORGANISMS AND THE USE THEREOF

[75] Inventors: Wolf-Dieter Henkels, Edingen-Neckarh; Marion Balzer, Neckarbischofsheim, both of Fed. Rep. of Germany

[73] Assignee: Grace Service Chemicals GmbH, Heidelberg, Fed. Rep. of Germany

[21] Appl. No.: 780,784

[22] Filed: Sep. 27, 1985

[30] Foreign Application Priority Data

Oct. 9, 1984 [DE] Fed. Rep. of Germany ....... 3436989

[51] Int. Cl.$^4$ ..................... A01N 37/34; A01N 43/26
[52] U.S. Cl. .................................... 514/441; 162/161; 210/764; 514/528
[58] Field of Search ................ 514/441, 528; 162/161; 210/764

[56] References Cited

U.S. PATENT DOCUMENTS

| | | | |
|---|---|---|---|
| 3,930,015 | 12/1975 | Swered et al. | 514/528 |
| 4,232,041 | 11/1980 | Burk et al. | 514/528 |
| 4,289,581 | 9/1981 | Katayama et al. | 514/441 |
| 4,466,975 | 8/1984 | Magami et al. | 514/373 |
| 4,518,610 | 5/1985 | Umekawa et al. | 514/516 |
| 4,647,577 | 3/1987 | Umekawa et al. | 514/441 |

OTHER PUBLICATIONS

Wolf et al., "2,2-Dibromo-3-Nitrilopropionamide, a Compound With Slimicidal Activity", *Applied Microbiology,* vol. 24, No. 4, pp. 581–584, (Oct. 1972).

*Primary Examiner*—Allen J. Robinson
*Attorney, Agent, or Firm*—Steven T. Trinker

[57] ABSTRACT

A composition killing or inhibiting the growth of microorganisms is described and which contains a mixture of 4,5-dichloro-1,2-dithiol-3-one and dibromonitrilopropionamide. The combination leads to a marked synergistic action of the two active substance components in the control of microorganisms. The composition is suitable for use in a large number of industrial systems.

8 Claims, 3 Drawing Sheets

COMPOSITION KILLING OR INHIBITING THE GROWTH OF MICROORGANISMS AND THE USE THEREOF

The present invention relates to a composition which kills or inhibits the growth of microorganisms and the use thereof.

The attack by microorganisms of industrial materials and water systems leads to numerous problems. For example, in the case of process water used in paper manufacture, as well as in cooling water systems, a microorganism slime is formed, which prejudices the manufacturing process or reduces the cooling capacity of the system. In addition, various industrial materials, such as e.g. heavy oil sludge, cutting oils, textile oils and the like are attacked by microorganisms, so that there are considerable quality losses. The same problems occur in the production and processing of foods, for example in the production of sugar.

JA-OS 52-14294 discloses the treatment of industrial water systems, particularly the process water used in paper manufacture as well as cooling water systems, with 4,5-dichloro-1,2-dithiol-3-one (DDO), in order to counteract the slime formation caused by microorganisms.

DE-OS 30 24 911 discloses the use of 4,5-dichloro-1,2-dithiol-3-one in conjunction with haloacetates. The combination of these constituents leads to a synergistic effect in the control of microorganism growth in industrial water systems and materials.

DE-OS 31 49 008 also describes microbicidal compositions for the treatment of industrial systems. The compositions contain 4,5-dichloro-1,2-dithiol-3-one and an alkylene-bis-thiocyanate, said constituents also having a synergistic activity in the control of microorganisms growth.

DE-OS 32 13 106 further discloses the synergistic activity of 4,5-dichloro-1,2-dithiol-3-one and 1,2-benzisothiazolin-3-one.

The antimicrobial activity of halogenated amides such as dibromonitrilopropionamide (DBNPA) is also known, cf. Wolff et al., "2,2-dibromo-3-nitrilopropionamide, A Compound with Slimicidal Activity", Appl. Microbiology, vol. 24, pp. 581 to 584, 1972. A stable aqueous composition with a content of DBNPA as the active substance is described in U.S. Pat. No. 4,232,041.

Although DBNPA has a broad action spectrum, it must be used in relatively high concentrations.

The problem of the present invention is to provide a microbicidal agent for the treatment of a large number of industrial materials and water systems, which has an intense activity when used in low active substance concentration.

For solving the set problem, the composition which kills or inhibits the growth of microorganisms according to claim 1 is proposed.

It has surprisingly been found that on combining DDO and DBNPA a marked synergistic activity of the two constituents is obtained in the control of microorganisms causing problems in industrial systems and simultaneously the antimicrobial action spectrum of the combination is considerably broadened compared with that of the individual constituents.

The synergistic effect of the two active substances combined according to the invention is largely independent of the particular mixing ratio. Thus, it has been found that this effect occurs equally well with a DDO:DBNPA weight ratio of 9:1 or 1:9 (cf. FIG. 1). The DDO:DBNPA mixing ratio is preferably approximately 4:1 or 4:1 parts by weight.

The composition is used in liquid form and the active substances can be dissolved or dispersed in the liquid carrier.

Preferably hydrophilic organic solvents providing storable stable compositions are used for dissolving the active substances. Examples of such solvents are amides such as dimethyl formamide, glycols such as ethylene glycol, propylene glycol, butyl glycol, diethylene glycol, dipropylene glycol, glycol ethers such as diethylene glycol monomethyl ether or ethylene glycol butyl ether. It is also possible to use mixtures of two or more of the aforementioned solvents.

The hydrophilic organic solvents can be wholly or partly replaced by water in the composition according to the invention. In this case, the active substances are in dispersion and the composition is stabilized by adding stabilizers, as well as dispersing and/or emulsifying agents.

The addition of a dispersing agent is also necessary if the composition according to the invention is used for the treatment of aqueous systems, in order to facilitate and improve the distribution of the composition in the system.

Preferred dispersing agents are cationic, anionic, nonionic or amphoteric surfactants, particular preference being given to nonionic and anionic surfactants. Examples of suitable nonionc agents are higher alcoholethylene oxide-(EO)-adducts, alkyl phenol-EO-adducts, propylene oxide-EO-adducts, as well as polyglycol ethers and/or esters. Examples of anionic surfactants are alkyl benzene sulphonates, secondary alkane sulphonates, olefin sulphonates, fatty alcohol sulphates and fatty alcohol ether sulphates.

According to a preferred embodiment, the composition according to the invention is prepared in that the active substances are dissolved in a hydrophilic organic solvent and the desired dispersing agent is added accompanied by stirring until a homogeneous solution is obtained. Alternatively the active substances can be dispersed in a mixture of a hydrophilic organic solvent and water, or in water alone, whilst the composition can be stabilized by adding a dispersing agent and known stabilizers.

The total quantity of the active substance mixture in the finished composition is preferably approximately 5 to 25% by weight, but contents up to approximately 50% by weight are possible.

The composition according to the invention can be used in the most varied industrial fields. It can be used for cooling water treatment and for water treatment in the paper industry. It can also be used as a preservative, e.g. in aqueous dispersions, oil sludges, cutting oils, paints and the like.

The composition according to the invention is particularly suitable for use in sugar manufacture, where there is a particular contamination risk during the extraction of the beet pulp in the diffusion tower. The agents according to the invention can be added to the extraction water in order to kill the microorganisms present.

The active substance quantities necessary for the treatment are dependent on the intended use. Normally the composition according to the invention is added to the system to be treated in quantities of approximately 2 to 400 ppm. In general, the dose of 2 to 20 ppm in the paper circuit water is adequate. Concentrations of 100 to 300 ppm and higher may be necessary in aqueous dispersions, particularly in the case of larger numbers of bacteria.

The invention is illustrated hereinafter by means of Examples.

EXAMPLE 1

The synergistic effect according to the invention was proved by the process of F. C. Kull P. C. Eismann, F. D. Sylvestrowicz and R. L. Mayer Applied Microbiology, vol. 9, pp. 538 to 541, 1961. *Escherichia coli* was used as the test organism.

(a) The bacteria culture was used in accordance with the conditions given in leaflet 44 of the leaflets dealing with the testing of packing agents (published by the working groups of the Industrievereinigung für Lebensmitteltechnologie und Verpackung e.V. at the Fraunhofer-Institut für Lebensmitteltechnologie und Verpackung, of the Munich Technical University).

(b) A two-dimensional dilution series was prepared, and the active substances components were contained in the particular dilution stage in the weight ratios given in Table 1. The minimum inhibiting concentration (MIC) was determined through using the agar suspension test for each dilution stage.

(c) The results are given in Table 1, in which $Q_a$ and $Q_b$ are the minimum inhibiting concentration of DDO or DBNPA in ppm when used alone, whilst $Q_A$ and $Q_B$ give the weight proportion of the particular active substance in the corresponding dilution stage containing the minimum inhibiting concentration of the mixture.

TABLE 1

| Wt. ratio A:B | $Q_a$ | $Q_A$ ppm | $Q_b$ | $Q_B$ | Mixture | $\frac{Q_A}{Q_a}$ | $\frac{Q_B}{Q_b}$ | $\frac{Q_A}{Q_a} + \frac{Q_B}{Q_b}$ |
|---|---|---|---|---|---|---|---|---|
| 100/0 | 13 | — | — | — | — | — | — | — |
| 80/20 | — | 6.4 | — | 1.6 | 8 | 0.49 | 0.06 | 0.55 |
| 60/40 | — | 6.0 | — | 4.0 | 10 | 0.46 | 0.16 | 0.62 |
| 50/50 | — | 5.0 | — | 5.0 | 10 | 0.38 | 0.20 | 0.58 |
| 40/60 | — | 3.2 | — | 4.8 | 8 | 0.25 | 0.19 | 0.44 |
| 20/80 | — | 2.6 | — | 10.4 | 13 | 0.20 | 0.42 | 0.62 |
| 0/100 | — | — | 25 | — | — | — | — | — |

In accordance with the aforementioned process a synergistic effect occurs if $$\frac{Q_A}{Q_a} + \frac{Q_B}{Q_b} < 1.$$

As can be gathered from the values in Table 1, each of the selected mixing ratios leads to a synergistic effect.

(d) In order to provide a better illustration, the results reproduced in Table 1 are shown graphically in FIG. 1. In this representation form, in the case of an additive effect of the active substances the values would appear on the lines between the minimum inhibiting concentrations of the individual active substances. The degree of downward deflection of the curve from a straight line is a measure of the synergistic effect of the active substances in the particular mixing ratio.

As is shown by FIG. 1, in the present test arrangement, the maximum synergistic effect is obtained at a DDO:DBNPA weight ratio of 40:60.

EXAMPLE 2

The process of Example 1 was repeated with the difference that the test organisms *Aspergillus niger* was used. The fungus culture was used in accordance with leaflet 43 of the leaflets relating to the testing of packing aids (loc. cit). The results are given in the following Table 2.

TABLE 2

| Wt. ratio A:B | $Q_a$ | $Q_A$ ppm | $Q_b$ | $Q_B$ | Mixture | $\frac{Q_A}{Q_a}$ | $\frac{Q_B}{Q_b}$ | $\frac{Q_A}{Q_a} + \frac{Q_B}{Q_b}$ |
|---|---|---|---|---|---|---|---|---|
| 100/0 | 6 | — | — | — | — | — | — | — |
| 80/20 | — | 3.2 | — | 0.8 | 4 | 0.533 | 0.04 | 0.5733 |
| 60/40 | — | 2.1 | — | 1.4 | 3.5 | 0.35 | 0.07 | 0.42 |
| 50/50 | — | 1.75 | — | 1.75 | 3.5 | 0.292 | 0.0875 | 0.3795 |
| 40/60 | — | 1.4 | — | 2.1 | 3.5 | 0.233 | 0.105 | 0.338 |
| 20/80 | — | 0.7 | — | 2.8 | 3.5 | 0.117 | 0.14 | 0.257 |
| 0/100 | — | — | 20 | — | — | — | — | — |

The results according to Table 2 are shown graphically in FIG. 2. It can be seen that the synergistic effect according to the invention also occurs when using *Aspergillus niger*.

EXAMPLE 3

The process of Example 1 was repeated with the different that a microorganism mixed culture isolated from the process water used in paper manufacture was used. The results are given in the following Table 3.

TABLE 3

| Wt. ratio A:B | $Q_a$ | $Q_A$ | $Q_B$ | $Q_b$ | Mixture | $\frac{Q_A}{Q_a}$ | $\frac{Q_B}{Q_b}$ | $\frac{Q_A}{Q_a} + \frac{Q_B}{Q_b}$ |
|---|---|---|---|---|---|---|---|---|
| 100/0 | 12.5 | — | — | — | — | — | — | — |
| 80/20 | — | 2 | — | 8 | 10 | 0.16 | 0.133 | 0.293 |
| 60/40 | — | 5 | — | 7.5 | 12.5 | 0.4 | 0.125 | 0.525 |
| 50/50 | — | 5 | — | 5 | 10 | 0.4 | 0.083 | 0.483 |
| 40/60 | — | 7.5 | — | 5 | 12.5 | 0.6 | 0.083 | 0.683 |
| 20/80 | — | 12 | — | 3 | 15 | 0.96 | 0.05 | 1.01 |

TABLE 3-continued

| Wt. ratio A:B | $Q_a$ | $Q_A$ | $Q_B$ | $Q_b$ | Mixture | $\frac{Q_A}{Q_a}$ | $\frac{Q_B}{Q_b}$ | $\frac{Q_A}{Q_a}+\frac{Q_B}{Q_b}$ |
| --- | --- | --- | --- | --- | --- | --- | --- | --- |
| 0/100 | — | — | 60 | — | — | — | — | — |

The results according to Table 3 are shown graphically in FIG. 3. The results show the marked synergistic effect of active substances DDO and DBNPA relative to the broad spectrum of microorganisms as present in the process water for paper manufacture as a typical industrial system.

I claim:

1. A composition for killing or inhibiting microorganisms in industrial materials or water systems comprising a mixture of 4,5-dichloro-1,2-dithiol-3-one (DDO) and dibromonitrilopropionamide (DBNPA) in amounts effective to provide a synergistic microbicidal activity.

2. A composition as defined in claim 1, wherein the DDO:DBNPA weight ratio of the mixture is from about 9:1 to 1:9.

3. A composition as defined in claim 1, wherein the DDO:DBNPA weight ratio of the mixture is from about 4:1 to 1:4.

4. A composition as defined in claims 1, 2, or 3, wherein the mixture of DDO and DBNPA is dissolved in an effective amount of an organic solvent.

5. A composition as defined in claims 1, 2, or 3, wherein the mixture of DDO and DBNPA is dispersed in a liquid carrier selected from the group consisting of an organic solvent, water and mixtures thereof together with an effective amount of an agent selected from the group consisting of dispersing agents, emulsifiers, stabilizers and mixtures thereof.

6. A composition as defined in claim 5, wherein the mixture of DDO and DBNPA comprises from about 5 to 25 weight percent of the mixture.

7. A method for inhibiting the growth of microorganisms or for killing microorganisms in industrial materials and water systems comprising adding from 2 to 400 ppm of the composition according to claim 1 to said industrial materials or water systems.

8. A method for preventing the contamination of beet sugar by microorganisms during the preparation of said beet sugar by a process wherein a beet pulp is extracted with water to extract sugar therefrom, comprising adding from 2 to 400 ppm of the composition according to claim 1 to the extraction water.

* * * * *